United States Patent [19]

Stewart

[11] Patent Number: 5,686,074
[45] Date of Patent: Nov. 11, 1997

[54] POISON IVY TREATMENT COMPOSITION AND METHOD OF USE

[76] Inventor: Ulvert H. Stewart, 10577 Daly Rd., Brooksville, Fla. 34601

[21] Appl. No.: 693,395

[22] Filed: Aug. 7, 1996

[51] Int. Cl.⁶ .......................... A61K 35/78; A61K 33/06
[52] U.S. Cl. ...................... 424/195.1; 424/698; 514/828; 514/862
[58] Field of Search .................. 424/195.1, 698; 514/828, 862

[56] References Cited

U.S. PATENT DOCUMENTS

| | | | |
|---|---|---|---|
| 3,023,144 | 2/1962 | Greathouse et al. | 514/164 |
| 3,519,711 | 7/1970 | Svigals | 424/659 |
| 4,025,645 | 5/1977 | Jelenko, III | 514/549 |
| 4,083,965 | 4/1978 | Bluhm | 424/602 |
| 4,353,896 | 10/1982 | Levy | 424/195.1 |

Primary Examiner—Irene Marx
Assistant Examiner—Janet M. Kerr
Attorney, Agent, or Firm—Allen, Dyer, Doppelt, Milbrath & Gilchrist, P.A.

[57] ABSTRACT

A composition and method are described for the treatment of allergic contact dermatitis, such as poison ivy, poison oak, and poison sumac. The composition includes linseed oil, an astringent such as alum powder, a starch such as cornstarch, an essential oil such as eucalyptus oil, and a citrus oil such as orange oil. The method includes applying the treatment composition to an affected area of skin, preferably once to twice per day.

3 Claims, No Drawings

POISON IVY TREATMENT COMPOSITION AND METHOD OF USE

BACKGROUND OF THE INVENTION

1. Field of the Invention

The present invention relates to compositions for the treatment of skin rashes, and, more particularly, to compositions for the treatment of poison ivy and related kinds of allergic contact dermatitis.

2. Description of Related Art

A poison ivy rash, which falls under the medical descriptor rhus dermatitis, is an allergic contact dermatitis caused by an exposure to plants of the genus Rhus (poison ivy, poison oak, poison sumac). These plants contain urushiol, a potent skin-sensitizing agent.

Several over-the-counter treatments are available to treat a poison ivy rash, including those containing calamine, which is a mixture of zinc oxide or zinc carbonate with a small amount of ferric oxide. Calamine is known to be an astringent.

In the patent literature compositions for the treatment of poison ivy have also been addressed. Examples include Greathouse et al. (U.S. Pat. No. 3,023,144), who disclose the use of citrus oil in a composition for topical application to infected or irritated skin. Svigals (U.S. Pat. No. 3,519,711) teaches an antipruritic composition that contains oil of geranium and Epsom salt (magnesium sulfate). The topical agent of Jelenko (U.S. Pat. No. 4,025,645) includes ethyl linoleate and monoisopropyl citrate. Bluhm (U.S. Pat. No. 4,083,965) discloses an anti-itch composition that comprises arrowroot (a starch) as an absorbent. The topical composition of Levy (U.S. Pat. No. 4,353,896) includes eucalyptus oil as a counterirritant.

SUMMARY OF THE INVENTION

It is therefore an object of the invention to provide a composition and method of use for the treatment of poison ivy and related forms of allergic contact dermatitis.

It is an additional object to provide such as composition that does not include asteroid component.

These objects and others are attained by the composition and method of use of the present invention.

The composition for the treatment of allergic contact dermatitis, such as the rashes caused by contact with poison ivy, poison oak, or poison sumac, comprises linseed oil, an astringent, a starch, an essential oil, and a citrus oil.

The method comprises the steps of preparing the treatment composition and applying it to an affected area of skin.

The features that characterize the invention, both as to organization and method of operation, together with further objects and advantages thereof, will be better understood from the following description. These and other objects attained, and advantages offered, by the present invention will become more fully apparent as the description that now follows is read.

DETAILED DESCRIPTION OF THE PREFERRED EMBODIMENTS

A description of the preferred embodiments of the present invention will now be presented.

A preferred embodiment of the composition is for the treatment of an allergic contact dermatitis caused by an exposure of human skin to urushiol. In this embodiment the composition comprises 3.8 volume percent linseed oil, 3.8 volume percent alum powder, 90.6 volume percent cornstarch, 1 volume percent eucalyptus oil, and 0.5 volume percent orange oil.

The proportions given above are intended to be exemplary and not to be limiting. One skilled in the art would be aware that slight deviations from these ranges would not hinder the efficacy of the invention.

Linseed oil is an oil extracted from flax seed, and is typically used in products such as paints and soaps. It has also been used as a remedy for burns, bruises, and blisters.

Alum powder is a potassium aluminum sulfate or an ammonium aluminum sulfate that is used as an astringent or styptic.

Eucalyptus oil is classified as one of the "essential" or "volatile" oils, which are not actually oils, but are extracted from their source, generally with steam. Eucalyptus oil is distilled from eucalyptus leaves, and is known for its use in expectorants and inhalants.

Orange oil is obtained from the orange peel.

The method of using the above composition comprises the steps of preparing the composition and applying it to an affected area of skin. The treatment has been found to be most effective when undertaken as soon as possible after exposure to the irritant.

Preferably, the treatment composition is applied once or twice per day until the rash disappears. In tests of the treatment, no harmful side effects have been experienced.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the composition and method of use described herein are by way of example, and the scope of the invention is not limited to the exact details of the composition.

Having now described the invention and the operation and use of a preferred embodiment thereof, and the advantageous new and useful results obtained thereby, the new and useful compositions, and reasonable chemical equivalents thereof obvious to those skilled in the art, are set forth in the appended claims.

What is claimed is:

1. A composition for the treatment of allergic contact dermatitis caused by contact of human skin with urushiol, consisting essentially of 3.8 volume percent linseed oil, 3.8 volume percent alum powder, 90.6 volume percent cornstarch, 1 volume percent eucalyptus oil, and 0.5 volume percent orange oil.

2. A method for treating allergic contact dermatitis caused by contact of human skin with urushiol comprising the steps of:

(1) preparing a treatment composition consisting essentially of 3.8 volume percent linseed oil, 3.8 volume percent alum powder, 90.6 volume percent cornstarch, 1 volume percent eucalyptus oil and 0.5 volume percent orange oil by mixing said ingredients and (2) applying a therapeutically effective amount of said treatment composition to an area of human skin affected with allergic contact dermatitis caused by contact of human skin to urushiol.

3. The method of claim 2 wherein said treatment composition is applied with a frequency of between one and two times per day.

* * * * *